United States Patent
Alakhov et al.

(10) Patent No.: US 9,919,053 B2
(45) Date of Patent: Mar. 20, 2018

(54) CABAZITAXEL COMPOSITION

(71) Applicant: SUPRATEK PHARMA INC., Pointe-Claire, Quebec (CA)

(72) Inventors: Valery Alakhov, Ile Bizard (CA); Grzegorz Pietrzynski, Montreal (CA); Kishore Patel, Pierrefonds (CA)

(73) Assignee: SOFTKEMO PHARMA CORP., Montreal (CA)

(*) Notice: Subject to any disclaimer, the term of this patent is extended or adjusted under 35 U.S.C. 154(b) by 0 days.

(21) Appl. No.: 14/655,214

(22) PCT Filed: Dec. 23, 2013

(86) PCT No.: PCT/IB2013/003255
§ 371 (c)(1),
(2) Date: Jun. 24, 2015

(87) PCT Pub. No.: WO2014/122498
PCT Pub. Date: Aug. 14, 2014

(65) Prior Publication Data
US 2015/0328321 A1    Nov. 19, 2015

Related U.S. Application Data

(60) Provisional application No. 61/848,172, filed on Dec. 24, 2012.

(51) Int. Cl.
| | | |
|---|---|---|
| *A61K 31/337* | (2006.01) | |
| *A61K 47/40* | (2006.01) | |
| *A61K 9/00* | (2006.01) | |
| *A61K 9/19* | (2006.01) | |
| *A61K 9/08* | (2006.01) | |
| *A61K 47/69* | (2017.01) | |

(52) U.S. Cl.
CPC ............ *A61K 47/40* (2013.01); *A61K 9/0019* (2013.01); *A61K 9/08* (2013.01); *A61K 9/19* (2013.01); *A61K 31/337* (2013.01); *A61K 47/6951* (2017.08)

(58) Field of Classification Search
CPC . A61K 31/337; A61K 47/40; A61K 47/48969
See application file for complete search history.

(56) References Cited

U.S. PATENT DOCUMENTS

| | | | |
|---|---|---|---|
| 2006/0258537 A1* | 11/2006 | Stella | A61K 31/724 504/291 |
| 2010/0041625 A1* | 2/2010 | Ren | A61K 31/337 514/58 |
| 2010/0048685 A1 | 2/2010 | Ren et al. | |
| 2010/0305202 A1* | 12/2010 | Hwang | A61K 9/19 514/449 |
| 2012/0058971 A1 | 3/2012 | Crawford et al. | |
| 2012/0065255 A1* | 3/2012 | Palepu | A61K 9/0019 514/449 |

FOREIGN PATENT DOCUMENTS

| | | |
|---|---|---|
| EP | 2075010 A1 | 7/2009 |
| JP | 200522989 | 1/2005 |
| JP | 5087086 | 2/2010 |
| WO | 2013024495 A1 | 2/2013 |

OTHER PUBLICATIONS

Hamada et al. Journal of Bioscience and Bioengineering, 2006, vol. 102, No. 4, pp. 369-371.*
Luke DR1, Tomaszewski K, Damle B, Schlamm HT. J Pharm Sci. Aug. 2010; 99(8):3291-301. doi: 10.1002/jps.22109. Review of the basic and clinical pharmacology of sulfobutylether-beta-cyclodextrin (SBECD).
Notification of Reasons for Rejection, Japanese Office Action, dated Nov. 14, 2017.

* cited by examiner

*Primary Examiner* — James D. Anderson
(74) *Attorney, Agent, or Firm* — Porzio Bromberg & Newman P.C.

(57) ABSTRACT

The present invention is directed to a composition comprising (a) cabazitaxel and (b) sulfobutyl ether beta cyclodextrin. Such composition exhibits unexpectedly desirable stability in aqueous media, permitting therapeutic dosages of the drug to be administered without the use of either ethanol or surfactants.

8 Claims, No Drawings

CABAZITAXEL COMPOSITION

FIELD OF THE INVENTION

The present invention is directed to a composition comprising (a) cabazitaxel and (b) sulfobutyl ether beta cyclodextrin. Such composition exhibits unexpectedly desirable stability in aqueous media, thus permitting therapeutic dosages of the drug to be administered without need of ethanol and surfactants.

BACKGROUND OF THE INVENTION

Cabazitaxel, (1S,2S,3R,4S,7R,9S,10S,12R,15S)-4-(Acetyloxy)-15-{[(2R,3S)-3-{[(tert-butoxy)carbonyl]amino}-2-hydroxy-3-phenylpropanoyl]oxy}-1-hydroxy-9,12-dimethoxy-10,14,17,17-tetramethyl-11-oxo-6-oxatetracyclo[11.3.1.$0^{3,10}$.$0^{4,7}$]heptadec-13-ene-2-yl benzoate, is a microtubule inhibitor which is being investigated for a number of cancer treatments, including head and neck cancer, non-small cell lung cancer (NSCLC), small cell lung cancer (SCLC), glioma, bladder cancer, gastric and esophageal cancer, breast cancer and ovarian cancer. Cabazitaxel has been specifically designed to overcome multi-drug resistance (MDR) associated with paclitaxel and docetaxel and with many other anticancer drugs.

Due to its poor solubility in water, the commercial formulation of cabazitaxel (JEVTANA®) employs polysorbate 80 (a surfactant) as a solubilizer and ethanol as a diluent. Due to the presence of such surfactant and ethanol this formulation requires that a patient be premedicated with an antihistamine, a corticosteroid and an $H_2$ antagonist. Such formulation further requires a two-step preparation process prior to infusion into a patient. In the first step a vial containing cabazitaxel and an excipient must be mixed with another vial containing ethanol; in the second step, this mixed solution is then diluted with saline or 5% dextrose. According to its label, the JEVTANA® dosing solution must be used within eight hours at room temperature, or within 24 hour if refrigerated. Both time limits include infusion time of approximately 1 hour.

Accordingly, it would be desirable to possess a cabazitaxel formulation which exhibited increased stability; which did not require the presence of surfactant and/or ethanol; and which could be prepared in a more simple and convenient process.

While the prior art has proposed the formulation of related compounds, such as docetaxel with substituted cyclodextrins, such formulations still contain ethanol. Thus, for example, Young et al (U.S. Pat. No. 8,481,511) disclose inclusion complexes of docetaxel and hydroxypropyl-beta-cyclodextrin or sulfobutyl-beta-cyclodextrin in a ratio of 1:10-150. The complexes are prepared as follows: docetaxel dissolved in ethanol is added into water solution of cyclodextrin via stirring, until docetaxel is completely dissolved; said solution is filtered in 0.2-04 μm microporous membrane then ethanol is removed through reduced pressure to obtain the inclusion complex in a liquid form; or ethanol, followed by water is removed through reduced pressure, then dried to obtain the inclusion complex in a solid form. Young et al stress the benefits of the reduced ethanol concentration in their final compositions stating that the "low residual ethanol level provided a favorable guarantee for improving the docetaxel stability and reducing irritation and other side effects". Consequently, it is unexpected that an improved formulation of cabazitaxel could be prepared using sulfobutyl ether beta cyclodexctrin which formulation did not contain any residual ethanol.

DESCRIPTION OF THE INVENTION

The present invention is directed to a composition comprising (a) cabazitaxel and (b) sulfobutyl ether beta cyclodextrin ("SBECD").

Typically, the weight ratio of cabazitaxel to SBECD is between 1:30 and 1:1000; preferably, such ratio is between 1:90 and 1:200. In one particularly preferred embodiment the composition of this invention comprises cabazitaxel and SBECD in weight ratio around 1:133.

Such composition may optionally further comprise additional components added to improve its pharmaceutical properties. In particular, an acid, a base, and/or a salt can be added to the composition to adjust the pH and the tonicity of the composition. It is particularly preferred that HCl, NaOH, citric acid and NaCl are used to adjust the pH and the tonicity of the composition.

In certain embodiments the composition is a sterile liquid aqueous solution suitable for administration by intravenous injection or infusion and comprises between 0.5% and 70% SBECD, preferably between 1% and 40% SBECD, and more preferably between 2% and 20% SBECD.

In other embodiments the composition of this invention is in the form of sterile solid lyophilizate or in the form of an aqueous solution comprising between 2% and 70% SBECD, preferably between 20% and 60%; both of which forms are suitable for storage.

The compositions of this invention may be prepared by mixing cabazitaxel with an aqueous solution of SBECD. Such compositions are typically mixed at room temperature, although higher or lower temperatures may be employed. The mixture is then typically filtered and stored. If desired the filtered solution may be freeze dried for storage.

EXAMPLES

Example 1. Cabazitaxel Solubility in Aqueous SBECD

Excess of cabazitael was mixed with aqueous SBECD solutions for 16 hours at 23° C. The resulting suspension was filtered through a 0.22 μm filter, and the clear filtrate solution was analyzed by HPLC. The concentration of cabazitaxel in solutions is presented in the table below.

TABLE

Equilibrium solubility of cabazitaxel in aqueous SBECD at 23° C.

| SBECD concentration [%] | Cabazitaxel concentration [mg/mL] |
| --- | --- |
| 40 | 4.17 |
| 20 | 2.28 |
| 10 | 0.99 |
| 2 | 0.46 |
| 1 | 0.27 |

Example 2. Stability of Solution of Cabazitaxel in Aqueous SBECD

A solution containing 2.02 mg/mL cabazitaxel in 20% aqueous SBECD was prepared by sequential dissolving SBECD in water, and cabazitaxel in the resulting solution, followed by filtration through a 0.22 μm filter. Portions of the solution was subsequently diluted with water to form three solutions having the cabazitaxel concentration listed in the Table below, respectively. The solutions were incubated at temperature 23° C. and at selected time points were analyzed using the HPLC. The results are presented in the table below. All solutions were stable.

TABLE

Cabazitaxel concentration in aqueous compositions with SBECD using different dilutions

| Time [hours] | Cabazitaxel concentration [mg/mL] | | |
|---|---|---|---|
| 0 | 0.098 | 0.268 | 0.510 |
| 11 | 0.099 | 0.268 | 0.515 |
| 24.5 | 0.099 | 0.269 | 0.518 |
| 36 | 0.098 | 0.268 | 0.512 |
| 45 | 0.098 | 0.268 | 0.517 |
| 100 | 0.097 | 0.263 | 0.512 |
| 120 | 0.097 | 0.266 | 0.518 |

Example 3. Preparation of Solution of Cabazitaxel in 20% Aqueous SBECD 2180 mg of SBECD was dissolved in 8707 mg of distilled water. 16.4 mg cabazitaxel was added into this solution and mixed until completely dissolved. The solution was filtered through a 0.22 μm filter.

Example 4. Preparation of Lyophilized Composition of Cabazitaxel and SBECD

The solution of the Example 3 was frozen quickly using dry ice. The frozen material was freeze dried.

Example 5. Reconstitution of Cabazitaxel Composition in Isotonic NaCl Solution 9.80 mL of 0.9% aqueous NaCl was added to 200 mg of the lyophilized composition of the Example 3. The mixture was gently mixed to produce clear a solution comprising 0.15 mg/mL cabazitaxel solution in 2% SBECD with 0.9% NaCl.

Example 6. Pharmacokinetics

Female Sprague-Dawley rats, 8 animals per group, received 1 hour i.v. infusion of solution of the Example 3, or solution comprising cabazitaxel, polysorbate 80, ethanol and water, equivalent to the commercial composition of cabazitaxel. Both compositions were administered at the dose 8 mg/kg. Blood samples were collected at 0.5, 1, 1.08, 1.25, 1.5, 2, 3, and 4 hours post beginning of the infusion; three samples from each animal were taken during the sampling. Plasma levels of cabazitaxel in each sample were determined using HPLC. The results are presented in the table below.

The results demonstrate that the solution of the Example 3 and the solution equivalent to the commercial composition of cabazitaxel provide equivalent exposure to cabazitaxel.

| | Cabazitaxel concentration in plasma [μg/mL] | | | |
|---|---|---|---|---|
| Time | Solution of the Example 3 | | cabazitaxel, polysorbate 80, ethanol and water | |
| [hours] | Mean | SEM | Mean | SEM |
| 0 | | | | |
| 0.5 | 0.86 | 0.38 | 1.14 | 0.47 |
| 1 | 2.18 | 0.05 | 1.80 | 0.17 |
| 1.08 | 0.86 | 0.17 | 1.05 | 0.02 |
| 1.25 | 0.79 | 0.19 | 0.69 | 0.10 |
| 1.5 | 0.76 | 0.04 | 0.48 | 0.11 |
| 2 | 0.42 | 0.09 | 0.52 | 0.21 |
| 3 | 0.29 | 0.15 | 0.38 | 0.21 |
| 4 | 0.27 | 0.27 | 0.21 | 0.02 |

Example 7. Efficacy in 3LL Model

C57BL/6 mice were inoculated i.v. with murine 3LL cells (200,000) and treated with i.v. injection of 10 mg/kg of solution of the Example 3, or solution comprising cabazitaxel, polysorbate 80, ethanol and water, equivalent to the commercial composition of cabazitaxel, on day 1, 4 and 7 after inoculation. Saline injection was used in the control group. Mice body weights were recorded to evaluate tolerability to the treatment. No mortalities were recorded. The animals were sacrificed on day 18 and the metastases in lungs were counted. The results are presented in the table below.

| | Control | | Solution of the Example 3 | | cabazitaxel, polysorbate 80, ethanol and water | |
|---|---|---|---|---|---|---|
| | Body weight [g] | | | | | |
| Day | Mean | SEM | Mean | SEM | Mean | SEM |
| 1 | 17.1 | 0.2 | 16.8 | 0.2 | 16.7 | 0.3 |
| 3 | 17.7 | 0.3 | 17.7 | 0.3 | 17.6 | 0.2 |
| 4 | 17.9 | 0.3 | 17.9 | 0.3 | 18.0 | 0.3 |
| 7 | 18.3 | 0.3 | 17.4 | 0.4 | 17.3 | 0.5 |
| 9 | 18.2 | 0.3 | 17.2 | 0.4 | 16.8 | 0.6 |
| 11 | 18.5 | 0.3 | 17.1 | 0.6 | 16.9 | 0.8 |
| 14 | 18.5 | 0.4 | 18.0 | 0.5 | 18.2 | 0.5 |
| Metastasis count | 78.4 | 10.0 | 10.6 | 1.4 | 21.0 | 4.6 |

Example 8. Efficacy in MDA-MB 231 Model

MDA-MB-231 cells (500,000 cells per site) in cell culture medium containing 30% Matrigel were subcutaneously inoculated at 2 sides of the flank (in the mid-flank) of nude Balb/c mice. After 16 days, when tumors reached 0.5-0.8 cm, the animals were randomly divided to three groups and treated on day 1, 4 and 7 with saline (control) or with 7.5 mg/kg of solution of the Example 3, or solution comprising cabazitaxel, polysorbate 80, ethanol and water, equivalent to the commercial composition of cabazitaxel. The tumor sizes and body weights were recorded during study, and tumors were removed and weighted upon study termination. The results are presented in the tables below.

|  | Control | | Solution of the Example 3 | | cabazitaxel, polysorbate 80, ethanol and water | |
|---|---|---|---|---|---|---|
| Day | Mean | SEM | Mean | SEM | Mean | SEM |
| Tumor volume [cm³] | | | | | | |
| 0 | 0.105 | 0.012 | 0.107 | 0.013 | 0.111 | 0.015 |
| 4 | 0.167 | 0.014 | 0.140 | 0.016 | 0.128 | 0.021 |
| 6 | 0.246 | 0.024 | 0.152 | 0.021 | 0.143 | 0.022 |
| 8 | 0.322 | 0.030 | 0.157 | 0.024 | 0.148 | 0.021 |
| 12 | 0.550 | 0.060 | 0.156 | 0.024 | 0.149 | 0.021 |
| 14 | 0.652 | 0.064 | 0.136 | 0.023 | 0.150 | 0.022 |
| 18 | 0.950 | 0.111 | 0.129 | 0.024 | 0.141 | 0.022 |
| 21 | 1.319 | 0.170 | 0.117 | 0.022 | 0.132 | 0.020 |
| Tumor weight [mg] | | | | | | |
| 21 | 891.3 | 106.5 | 39.6 | 7.7 | 34.0 | 8.9 |
| Body weight [g] | | | | | | |
| 1 | 17.8 | 0.2 | 18.2 | 0.4 | 17.6 | 0.4 |
| 4 | 18.0 | 0.1 | 17.9 | 0.4 | 17.1 | 0.5 |
| 6 | 18.2 | 0.2 | 17.7 | 0.4 | 16.9 | 0.5 |
| 7 | 18.0 | 0.2 | 17.6 | 0.4 | 16.7 | 0.4 |
| 8 | 18.3 | 0.2 | 17.5 | 0.3 | 16.7 | 0.4 |
| 12 | 18.7 | 0.2 | 17.4 | 0.5 | 16.1 | 0.3 |
| 14 | 18.5 | 0.1 | 17.3 | 0.5 | 16.7 | 0.3 |
| 18 | 18.9 | 0.1 | 18.4 | 0.6 | 17.5 | 0.4 |
| 21 | 19.2 | 0.3 | 18.8 | 0.5 | 18.4 | 0.4 |

Example 9. Efficacy in DU-145 Model

Human prostate carcinoma DU-145 cells (2,000,000 cells per site) in cell culture medium containing 50% Matrigel were subcutaneously inoculated at 2 sides of the mid-flank of SCID mice. After 21 days (when tumors reached 0.5-0.8 cm) the animals were randomly divided to three groups and treated on day 1, 4 and 7 after that with saline (control) or with 7.5 mg/kg of solution of the Example 3, or solution comprising cabazitaxel, polysorbate 80, ethanol and water, equivalent to the commercial composition of cabazitaxel. The tumor sizes and body weights were recorded. The results are presented in the tables below.

|  | Control | | Solution of the Example 3 | | cabazitaxel, polysorbate 80, ethanol and water | |
|---|---|---|---|---|---|---|
| Day | Mean | SEM | Mean | SEM | Mean | SEM |
| Tumor volume [cm³] | | | | | | |
| 0 | 0.156 | 0.025 | 0.157 | 0.024 | 0.156 | 0.021 |
| 4 | 0.242 | 0.036 | 0.199 | 0.032 | 0.191 | 0.027 |
| 7 | 0.493 | 0.095 | 0.206 | 0.041 | 0.200 | 0.029 |
| 11 | 0.760 | 0.139 | 0.155 | 0.040 | 0.171 | 0.028 |
| 14 | 1.732 | 0.241 | 0.138 | 0.039 | 0.144 | 0.032 |
| 18 | 1.434 | 0.247 | 0.109 | 0.021 | 0.122 | 0.028 |
| 21 |  |  | 0.107 | 0.019 | 0.109 | 0.023 |
| 26 |  |  | 0.107 | 0.014 | 0.104 | 0.022 |
| 29 |  |  | 0.108 | 0.013 | 0.103 | 0.022 |
| 33 |  |  | 0.127 | 0.016 | 0.128 | 0.026 |

|  | Control | | Solution of the Example 3 | | cabazitaxel, polysorbate 80, ethanol and water | |
|---|---|---|---|---|---|---|
| Day | Mean | SEM | Mean | SEM | Mean | SEM |
| Body weight [g] | | | | | | |
| 1 | 26.6 | 0.7 | 26.8 | 0.8 | 30.5 | 0.9 |
| 4 | 27.1 | 0.8 | 27.0 | 0.6 | 30.8 | 0.8 |
| 7 | 27.2 | 0.7 | 26.0 | 0.6 | 29.4 | 1.0 |
| 11 | 27.7 | 1.0 | 23.2 | 0.7 | 26.3 | 1.0 |
| 14 | 27.9 | 0.9 | 23.1 | 0.6 | 25.9 | 0.9 |
| 18 |  |  | 24.8 | 0.5 | 28.3 | 0.9 |
| 21 |  |  | 25.4 | 0.6 | 29.7 | 0.9 |
| 26 |  |  | 26.7 | 0.7 | 30.2 | 1.0 |
| 29 |  |  | 26.5 | 0.6 | 30.2 | 0.9 |
| 33 |  |  | 27.5 | 0.7 | 31.3 | 1.0 |

What is claimed is:

1. An aqueous composition comprising: (a) cabazitaxel and (b) sulfobutylether beta-cyclodextrin, wherein such composition (i) does not contain any ethanol and (ii) exhibits an equilibrium solubility of cabazitaxel of at least 0.27 mg/mL at 23° C.

2. The composition of claim 1 wherein said composition is in the form of an aqueous solution comprising between 1% and 40% sulfobutylether beta-cyclodextrin by weight.

3. The composition of claim 2 wherein said composition is in the form of an aqueous solution comprising between 2% and 20% sulfobutylether beta-cyclodextrin by weight.

4. A solid lyophilizate formed from the composition of claim 1.

5. The composition of claim 1 wherein such composition does not contain any surfactant.

6. The composition of claim 1 wherein the composition exhibits an equilibrium solubility of cabazitaxel of between 0.27 and 4.17 mg/mL.

7. The composition of claim 6 wherein the composition exhibits an equilibrium solubility of cabazitaxel of between 0.46 and 4.17 mg/mL.

8. The composition of claim 7 wherein the composition exhibits an equilibrium solubility of cabazitaxel of between 0.99 and 4.17 mg/mL.

\* \* \* \* \*